(12) United States Patent
Kikuchi et al.

(10) Patent No.: US 7,153,938 B2
(45) Date of Patent: Dec. 26, 2006

(54) CROSS-LINKED APATITE/COLLAGEN POROUS BODY CONTAINING SELF-ORGANIZED APATITE/COLLAGEN COMPOSITE AND ITS PRODUCTION METHOD

(75) Inventors: Masanori Kikuchi, Ibaraki (JP); Junzo Tanaka, Ibaraki (JP); Hisatoshi Kobayashi, Ibaraki (JP); Daisuke Shoji, Tokyo (JP)

(73) Assignees: National Institute for Materials Science, Ibaraki (JP); PENTAX Corporation, Tokyo (JP)

( * ) Notice: Subject to any disclaimer, the term of this patent is extended or adjusted under 35 U.S.C. 154(b) by 0 days.

(21) Appl. No.: 11/123,203

(22) Filed: May 6, 2005

(65) Prior Publication Data

US 2005/0271695 A1    Dec. 8, 2005

Related U.S. Application Data

(63) Continuation-in-part of application No. PCT/JP03/13717, filed on Oct. 27, 2003.

(30) Foreign Application Priority Data

Nov. 6, 2002    (JP) .............................. 2002-322507

(51) Int. Cl.
*A61K 38/17* (2006.01)
(52) U.S. Cl. .................................................. 530/356
(58) Field of Classification Search ..................... None
See application file for complete search history.

(56) References Cited

U.S. PATENT DOCUMENTS

| | | | |
|---|---|---|---|
| 4,629,464 A | | 12/1986 | Takata et al. |
| 4,795,467 A | * | 1/1989 | Piez et al. .................. 424/423 |
| 5,215,941 A | | 6/1993 | Yasukawa |
| 5,776,193 A | | 7/1998 | Kwan et al. |
| 6,541,023 B1 | | 4/2003 | Andre et al. |
| 2002/0022885 A1 | | 2/2002 | Ochi |
| 2005/0004242 A1 | * | 1/2005 | Sotome et al. ................. 521/61 |
| 2005/0053638 A1 | * | 3/2005 | Tanaka et al. ............... 424/423 |

FOREIGN PATENT DOCUMENTS

| | | |
|---|---|---|
| JP | 61- 079463 | 4/1986 |
| JP | 6-304242 | 11/1994 |
| JP | 7- 101708 | 4/1995 |
| JP | 7- 101708 | 4/1995 |
| JP | 11-192081 | 7/1999 |
| JP | 11-199209 | 7/1999 |
| JP | 11- 199209 | 7/1999 |
| JP | 11199209 | * 7/1999 |
| JP | 11-513590 | 11/1999 |
| JP | 2000- 005298 | 1/2000 |
| JP | 2000-005298 | 1/2000 |
| JP | 2002- 102328 | 4/2002 |
| JP | 2003-190271 | 7/2003 |
| WO | 97/14376 | 4/1997 |
| WO | WO9714376 | * 4/1997 |
| WO | 01/92322 | 12/2001 |
| WO | 2004/103422 | 2/2004 |
| WO | 2004/ 103422 | 2/2004 |
| WO | 03/092759 | 11/2005 |

OTHER PUBLICATIONS

Horiguchi et al., Apatite-Collagen Complex. Preparation of a New Apatite-Collagen Complex. Shika Zairyo Kikai, 1990, vol. 6, pp. 863-870.*
English Language Abstract of JP 6-304242, 1994.
English Language Abstract of JP 11-192081, 1999.
English Language Abstract of JP 2003-190271, 2003.
Masanori Kikuchi et al., "Self-Organization Mechanism in a Bone-like Hyrdoxyapatite/Collagen Nanocomposite Synthesized in Vitro and its Biological Reaction in Vivo", Biomaterials, vol. 22, pp. 1705-1711 (2001).
U.S. Appl. No. 10/558,245, filed May 26, 2004, in named of Katsumi Kawamura et al.
Kikuchi M et al., "Self-Organization Mechanism in a Bone-Like Hydroxyapoatite/Collagen Nanocomposite Synthesized In Vitro and Its Biological Reaction In Vivo", Biomaterials, vol. 22, No. 13, pp. 1705-1711 (2001).
English Language Abstract of JP 2003-190271.
Ryuji Kato et al., "Toketsu Kansoho ni yoru Apatite no Kohaikosei Takotai no Sakusei," Dai 6 Kai Seitai Kanren Ceramics Toronkai Koen Yokoshu, 2002 Nen, p. 22.
Chang, M.C. et al., Preparation of a porous hydroxyapatite/collagen nanocomposite using glutaraldehyde as a crosslinking agent, Journal of Materials Science Letters, 2001, vol. 20, No. 13, pp. 1199-1201.
Ryuji Kato et al., "Toketsu Kansoho ni yoru Apatite no Kohaikosei Takotai no Sakusei," Dai 6 Kai Seitai Kanren Ceramics Toronkai Koen Yokoshu, 2002 Nen, p. 22.
Chang, M. C. et al., Preparation of a porous hydroxyapatite/collagen nanocomposite using glutaraldehyde as a crosslinking agent, Journal of Materials Science Letters, 2001, vol. 20, No. 13, pp. 1199-1201.
English language abstract of JP 7-101708, published Apr. 18, 1995.
English language abstract of JP 11-199209, published Jul. 27, 1999.
English language abstract of JP 2000-005298, published Jan. 11, 2000.

* cited by examiner

*Primary Examiner*—Robert A. Wax
(74) *Attorney, Agent, or Firm*—Greenblum & Bernstein, P.L.C.

(57) ABSTRACT

A method for producing a cross-linked apatite/collagen porous body comprising the steps of gelling and then freeze-drying a dispersion containing an apatite/collagen composite and collagen to form a porous body, and further cross-linking collagen in the porous body, and a cross-linked apatite/collagen porous body produced by this method.

13 Claims, No Drawings

CROSS-LINKED APATITE/COLLAGEN POROUS BODY CONTAINING SELF-ORGANIZED APATITE/COLLAGEN COMPOSITE AND ITS PRODUCTION METHOD

CROSS-REFERENCE TO RELATED APPLICATIONS

This application is a Continuation in Part of International Patent Application No. PCT/JP2003/013717, filed Oct. 27, 2003, the disclosure of which is expressly incorporated by reference herein in its entirety, and which published as WO 2004/041320 A1 on May 21, 2004, and claims priority of Japanese Patent Application No. 2002-322507, filed on Nov. 6, 2002.

FIELD OF THE INVENTION

The present invention relates to a cross-linked apatite/collagen porous body containing an apatite/collagen composite for use in artificial bone, cell scaffold, etc., and its production method.

BACKGROUND OF THE INVENTION

Because of excellent compatibility with human bone, artificial bone made of apatite can be bonded to the human bone directly. Accordingly, the artificial bone made of apatite has recently been appreciated for effectiveness, finding clinical applications in cosmetic surgery, neurosurgery, plastic surgery, oral surgery, etc. However, artificial ceramic bone such as apatite is not necessarily completely identical with human bone in terms of mechanical properties and physiological properties. For instance, a so-called artificial ceramic bone made only of apatite is harder and more brittle than the human bone. While the human bone is repeatedly subjected to metabolism of absorption and regeneration, the artificial bone made of apatite is not substantially dissolved but semi-permanently remains in human body. The remaining artificial bone breaks human bone at an interface with the human bone, making it likely to cause bone fracture.

Research has recently become active on artificial bone decomposable in the human body, which is closer in composition to human bone than the artificial apatite bone, and various proposals have been made. For instance, JP 11-513590 A discloses a cross-linked apatite/collagen porous body having a network structure, in which collagen and, if necessary, other binders are bonded to hydroxyapatite. Because this cross-linked apatite/collagen porous body is decomposable in human body, human bone is formed in the cross-linked apatite/collagen porous body, and the cross-linked apatite/collagen porous body per se is absorbed in a human body. Accordingly, this cross-linked apatite/collagen porous body can be used for the fixation of vertebra, the filling of bone defects, the repair of fractured bone and, the grafting of periodontal defects, etc. However, this cross-linked apatite/collagen porous body is a simple mixture of collagen and apatite, which does not have a living human bone structure, in which the C-axis of the apatite is oriented along collagen fibers. Further, this cross-linked apatite/collagen porous body has insufficient mechanical strength and poor bone neoplasia.

OBJECT OF THE INVENTION

Accordingly, an object of the present invention is to provide a cross-linked apatite/collagen porous body absorbed in a human body according to the same mechanism as in living human bone, and having high bone neoplasia, which can be used for artificial bone, etc., and its production method.

DISCLOSURE OF THE INVENTION

As a result of intense research in view of the above object, the inventors have found that when a dispersion containing an apatite/collagen composite and collagen is gelled before its freeze-drying, the resultant cross-linked apatite/collagen porous body has a uniform structure with high strength. The present invention has been completed based on this finding.

Thus, the method for producing a cross-linked apatite/collagen porous body according to the present invention comprises the steps of freeze-drying a dispersion containing an apatite/collagen composite and collagen to form a porous body, and then cross-linking collagen in the porous body, the dispersion being freeze-dried after gelation.

A ratio of the apatite/collagen composite to the collagen is preferably 97/3 to 93/7 by mass in the dispersion. An apatite/collagen ratio is preferably 9/1 to 6/4 by mass in the apatite/collagen composite.

In the gelation of the dispersion, the dispersion temperature is preferably kept at 35 to 43° C., and the dispersion preferably has pH of 6.8 to 7.6 and ionic strength of 0.2 to 0.8 before the gelation.

The apatite/collagen composite is preferably in the form of fibers as long as 0.01 to 1 mm. Apatite in the apatite/collagen composite preferably has a C-axis oriented along the collagen fibers. Apatite in the cross-linked apatite/collagen porous body also preferably has a C-axis oriented along the collagen fibers.

The cross-linked apatite/collagen porous body of the present invention is produced by any of the above methods.

BEST MODE FOR CARRYING OUT THE INVENTION

[1] Production of Apatite/Collagen Composite

In the production of the cross-linked apatite/collagen porous body of the present invention, an apatite/collagen composite and collagen as a binder are used as starting materials. The apatite/collagen composite preferably has a structure similar to that of a living human bone, in which hydroxyapatite and collagen are oriented in a self-organized manner. The term "self-organization" means that calcium hydroxyphosphate (hydroxyapatite) having an apatite structure has orientation peculiar to living human bone along collagen fibers, namely that the C-axis of the hydroxyapatite is in alignment with the collagen fibers.

(1) Starting Materials

The apatite/collagen composite is produced from collagen, phosphates and calcium salts as starting materials. Thought not particularly restricted, the collagen may be extracted from animals, etc. The kinds, parts, ages, etc. of the animals are not particularly restrictive. In general, collagen obtained from skins, bones, cartilages, tendons, internal organs, etc. of mammals such as cow, pig, horse, rabbit and rat and birds such as hen, etc. may be used. Collagen-like proteins obtained from skins, bones, cartilages, fins, scales, internal organs, etc. of fish such as cod, flounder, flatfish, salmon, trout, tuna, mackerel, red snapper, sardine, shark, etc. may also be used. The extraction method of collagen is not particularly restrictive but may be a usual one. In place of collagen extracted from animal tissues, collagen produced by gene recombination technologies may also be used.

Phosphoric acid or its salt [hereinafter referred to simply as "phosphoric acid (salt)"] includes phosphoric acid, disodium hydrogenphosphate, sodium dihydrogenphosphate, dipotassium hydrogenphosphate, potassium dihydrogenphosphate, etc. The calcium salts include calcium carbonate, calcium acetate, calcium hydroxide, etc. The phosphate and the calcium salt are preferably added in the form of a uniform aqueous solution or suspension.

The fiber length of the resultant apatite/collagen composite can be controlled by a mass ratio of the apatite starting material [phosphoric acid (salt) and calcium salt] and collagen used. Accordingly, the mass ratio of the apatite starting material and collagen used is properly determined depending on a targeted composition ratio of the apatite/collagen composite. A mass ratio of apatite to collagen in the apatite/collagen composite used in the method of the present invention is preferably 9/1 to 6/4, for instance, 8/2.

(2) Preparation of Solution

First, an aqueous phosphoric acid (salt) solution and an aqueous calcium salt solution or suspension are prepared. Though the concentrations of the aqueous phosphoric acid (salt) solution and the aqueous calcium salt solution or suspension are not particularly restrictive as long as the phosphoric acid (salt) and the calcium salt are at a desired ratio, it is preferable for the convenience of a dropping operation described later that the concentration of the aqueous phosphoric acid (salt) solution is 15 to 240 mM, for instance, about 120 mM, and that the concentration of the aqueous calcium salt solution or suspension is 50 to 800 mM, for instance, about 400 mM. Collagen is added to the above-described aqueous phosphoric acid (salt) solution generally in the form of an aqueous solution in phosphoric acid. An aqueous solution of collagen in phosphoric acid may contain collagen at a concentration of 0.1 to 1% by mass, for instance, about 0.85% by mass, and phosphoric acid at a concentration of 1 to 40 mM, for instance, about 20 mM.

(3) Production of Apatite/Collagen Composite

Water substantially in the same amount as that of the aqueous calcium salt solution or suspension to be added is charged into a reactor and heated to about 40° C. in advance. An aqueous phosphoric acid (salt) solution containing collagen and an aqueous calcium salt solution or suspension are simultaneously dropped thereinto. The fiber length of the synthesized apatite/collagen composite can be controlled by controlling dropping conditions. The dropping speed is preferably 1 to 60 ml/minute, for instance, about 30 ml/minute. The stirring speed is preferably 1 to 400 rpm, for instance, about 200 rpm.

The reaction solution is preferably kept at pH of 8.9 to 9.1. If the concentrations of the calcium ion and/or the phosphoric acid ion exceeded the above ranges, the self-organization of the composite would be hindered. The above dropping conditions provide the apatite/collagen composite with fiber length of 1 mm or less, suitable as a starting material for the cross-linked apatite/collagen porous body. The apatite/collagen composite is self-organized.

After completion of dropping, a slurry-like mixture of the apatite/collagen composite and water is freeze-dried. The freeze-drying is carried out by rapidly drying in vacuum in a frozen state at −10° C. or lower.

[2] Production of Cross-linked Apatite/Collagen Porous Body (1) Preparation of Dispersion Containing Apatite/Collagen Composite (2) Production of Dispersion Containing Apatite/Collagen Composite The apatite/collagen composite is mixed with a liquid such as water, an aqueous phosphoric acid solution, etc., and stirred to prepare a paste-like dispersion. The amount of the liquid added is preferably 80 to 99% by volume, more preferably 90 to 97% by volume, based on 100% by volume of the apatite/collagen composite. The resultant cross-linked apatite/collagen porous body has a porosity P, which depends on a volume ratio of the apatite/collagen composite to the liquid in the dispersion as represented by the following formula (1):

$$P=B/(A+B) \qquad (1),$$

wherein A represents the volume of the apatite/collagen composite in the dispersion, and B represents the volume of a liquid in the dispersion. Accordingly, it is possible to control the porosity P of the cross-linked apatite/collagen porous body by adjusting the amount of the liquid to be added. The porosity P is generally 88–99%, prefereably 90–97%. The fibrous apatite/collagen composite is cut by stirring the dispersion after adding the liquid, resulting in a larger fiber length distribution range, and thus providing the resultant cross-linked apatite/collagen porous body with improved strength.

The composite dispersion is mixed with collagen as a binder and further stirred. The amount of collagen added is preferably 1 to 10% by mass, more preferably 3 to 6% by mass, based on 100% by mass of the apatite/collagen composite. Like in the composite, collagen is preferably added in the form of an aqueous solution in phosphoric acid. Though the concentration, etc. of an aqueous solution of collagen in phosphoric acid is not particularly restrictive, the concentration of collagen is about 0.85% by mass, and the concentration of phosphoric acid is about 20 mM from the practical point of view.

(2) Gelation of Dispersion

Because the addition of an aqueous solution of collagen in phosphoric acid (salt) turns the dispersion acidic, an alkali solution such as a sodium hydroxide solution, etc. is added until the dispersion has pH of about 7. The pH of the dispersion is preferably 6.8 to 7.6, more preferably 7.0 to 7.4. By adjusting the pH of the dispersion to 6.8 to 7.6, it is possible to prevent collagen added as a binder from becoming gelatin in the gelation described later.

The dispersion is mixed with an about 10-times concentrated solution of a physiological buffer saline (PBS) of phosphoric acid and stirred to adjust the ionic strength of the dispersion to 0.2 to 0.8. The more preferred ionic strength is as large as about 0.8, on the same level as that of PBS. Increase in the ionic strength of the dispersion can accelerate collagen added as a binder to form fibers.

The dispersion charged into a cylindrical molding die having an inner diameter of 17 mm is kept at a temperature of 35 to 43° C. for gelation. The heating temperature is more preferably 35 to 40° C. For sufficient gelation of the dispersion, the heating time is preferably 0.5 to 3.5 hours, more preferably 1 to 3 hours. With the dispersion kept at 35 to 43°

C., the collagen added as a binder forms fibers, thereby turning the dispersion to a gel. The gelled dispersion can prevent the apatite/collagen composite from precipitating therein, thereby producing a uniform porous body. The dispersion subjected to the gelation is in a jelly-like state. A ball of 7 mm in diameter was pressed into the as-formed gel (height: 35 mm) in the cylindrical molding die at a speed of 0.5 mm/minute, to measure a stress that the ball received from the gel, which was compressed by the ball by 5 mm. The stress measured is called "gel strength". The gel strength is 0.01/0.5 N.

(3) Freeze-drying

After the gelation, the dispersion is frozen. The freezing temperature is preferably −80° C. to −10° C., more preferably −80° C. to −20° C. The size and shape of pores in the porous body can be controlled by a freezing speed. For instance, a larger freezing speed tends to provide smaller pore size to the resultant porous body. The porous body had an average pore size of 100–1000 μm. The freezing speed may be 0.0004–0.01° C./sec. For the porosity of 95%, and 0.00008–0.004° C./sec. for the porosity of 90%.

The dispersion is then freeze-dried to form a porous body. The freeze-drying is carried out by evacuating and rapidly drying in a frozen state at −10° C. or lower, as in the case of the composite. The freeze-drying needs only be conducted until the dispersion is sufficiently dried. Thought not particularly restricted, the freeze-drying time is generally about 24 to 72 hours.

(4) Cross-linking of Collagen

The cross-linking of collagen may be carried out by any methods such as physical cross-linking methods using γ-rays, ultraviolet rays, electron beams, thermal dehydration, etc., or chemical cross-linking methods using cross-linking agents, condensation agents, etc. In the case of the chemical cross-linking, the freeze-dried porous body is immersed in a cross-linking agent solution to cross-link collagen in the porous body.

The cross-linking agents may be, for instance, aldehydes such as glutaraldehyde, formaldehyde, etc.; isocyanates such as hexamethylene diisocyanate, etc.; carbodiimides such as a hydrochloric acid salt of 1-ethyl-3-(3-dimethylaminopropyl)carbodiimide; epoxies such as ethylene glycol diethyl ether, etc.; transglutaminase, etc. Among these cross-linking agents, glutaraldehyde is particularly preferable from the aspects of the easiness of controlling the degree of cross-linking and the compatibility of the resultant cross-linked apatite/collagen porous body with human body.

When glutaraldehyde is used as the cross-linking agent, the concentration of a glutaraldehyde solution is preferably 0.005 to 0.015% by mass, more preferably 0.005 to 0.01% by mass. The cross-linked apatite/collagen porous body should be dehydrated. When alcohol such as ethanol, etc. is used as a solvent for a glutaraldehyde solution, the dehydration of the cross-linked apatite/collagen porous body can be conducted simultaneously with the cross-linking of collagen. A cross-linking reaction occurs in a state where the apatite/collagen composite is contracted, by conducting the dehydration and the cross-linking simultaneously, so that the resultant cross-linked apatite/collagen porous body can have improved elasticity.

After the cross-linking, the cross-linked apatite/collagen porous body is immersed in aqueous solution of about 2% by mass of glycine to remove unreacted glutaraldehyde, and then washed with water. The cross-linked apatite/collagen porous body is further immersed in ethanol for dehydration, and then dried at room temperature.

[3] Properties and Applications of Cross-linked Apatite/Collagen Porous Body

The cross-linked apatite/collagen porous body of the present invention containing a self-organized apatite/collagen composite has higher water absorption properties and elasticity than those of conventional apatite cross-linked apatite/collagen porous bodies. It also exhibits elasticity in a water-containing state, thereby having excellent compatibility with human body and excellent bone conduction.

Because the above-described properties are preferable as a biomaterial, the cross-linked apatite/collagen porous body of the present invention, which is sterilized by γ rays, electron beams, dry-heating, etc., can be used as a bone-regenerating material as a substitute for a living human bone, etc. Specifically, it is suitable as artificial bone, artificial joints, materials for bonding tendon to bone, dental implants, etc.

The present invention will be explained in more detail with reference to Examples below without intention of restricting the scope of the present invention.

EXAMPLE 1

(A) Synthesis of Apatite/Collagen Composite 168 ml of a 120-mM aqueous phosphoric acid solution was added to 235 g of an aqueous solution of collagen in phosphoric acid (collagen concentration: 0.85% by mass, phosphoric acid concentration: 20 mM) and stirred, to prepare a diluted aqueous solution of collagen in phosphoric acid. 200 ml of a 400-mM calcium hydroxide suspension was also prepared. 200 ml of pure water was charged into a reactor, and heated to 40° C. The diluted aqueous solution of collagen in phosphoric acid and the calcium hydroxide suspension were simultaneously dropped into this reactor at a rate of about 30 ml/minute, and the resultant reaction solution was stirred at 200 rpm to prepare a slurry containing composite apatite/collagen fibers. The reaction solution was kept at pH of 8.9 to 9.1 during dropping. The resultant composite apatite/collagen fibers were as long as about 1 mm or less. The slurry containing the apatite/collagen composite was freeze-dried. A ratio of the apatite to the collagen in the apatite/collagen composite was 8/2 by mass.

(B) Preparation of Cross-linked Apatite/Collagen Porous Body 1 g of the freeze-dried apatite/collagen composite was added to 3.6 ml of pure water and stirred to form a paste-like dispersion. This paste-like dispersion was mixed with 4 g of an aqueous solution of collagen in phosphoric acid and stirred, and a 1-N aqueous NaOH solution was added until the pH reached about 7. A ratio of the apatite/collagen composite to the collagen was 97/3 by mass. Tenfold-concentrated PBS was then added to the dispersion until the ionic strength of the dispersion reached 0.8. The amount of a liquid (pure water+diluted aqueous solution of collagen in phosphoric acid+aqueous NaOH solution+PBS) added was 95% by volume of the apatite/collagen composite.

The resultant dispersion was charged into a molding die and kept at 37° C. for 2 hours for gelation, to obtain a jelly-like formed body. This formed body was frozen at −20° C., and then dried by a freeze dryer. The dried formed body was immersed in a solution of 0.01% by mass of glutaraldehyde in ethanol (concentration: 99.5%), and cross-linked at 25° C. for 1 hour to obtain a cross-linked apatite/collagen porous body. After washed with water, this cross-linked apatite/collagen porous body was immersed in a 2-%-by-mass aqueous glycine solution to remove unreacted glutaraldehyde, and then washed with water again. It was further immersed in ethanol (concentration: 99.5%) for dehydration, and then dried at room temperature. The resultant cross-linked apatite/collagen porous body had a porosity of 95%.

A rectangular-prism-shaped test piece of 5 mm×5 mm×10 mm was cut out of the resultant cross-linked apatite/collagen porous body, to measure its rupture strength at a stretching speed of 0.1 mm/second. As a result, the rupture strength of the cross-linked apatite/collagen porous body was about 0.8 N.

EXAMPLE 2

A cross-linked apatite/collagen porous body was produced in the same manner as in Example 1 except for changing the gelation temperature to 40° C., and measured with respect to porosity and rupture strength. As a result, the porosity was 95% and the rupture strength was about 0.8 N.

COMPARATIVE EXAMPLE 1

A cross-linked apatite/collagen porous body was produced in the same manner as in Example 1 except for conducting no gelation, and measured with respect to rupture strength. As a result, the rupture strength was about 0.4 N.

APPLICABILITY IN INDUSTRY

As described above in detail, the method of the present invention can produce a cross-linked apatite/collagen porous body containing a self-organized apatite/collagen composite, which has excellent compatibility with human body and excellent bone conduction, as well as large mechanical strength such as rupture strength, etc. The cross-linked apatite/collagen porous body having such properties is suitable as a biomaterial for artificial bone, artificial joints, etc. The present disclosure relates to subject matter contained in Japanese Patent Application No. 2002-322507 (filed on Nov. 6, 2002) which is expressly incorporated herein by reference in its entirety.

What is claimed is:

1. A method for producing a cross-linked apatite/collagen porous body comprising mixing an apatite/collagen composite with an aqueous solution of collagen in phosphoric acid or a salt thereof to form a dispersion; gelating the dispersion after adjusting pH of the dispersion to 6.8 to 7.6; freeze-drying the gelled dispersion to form a porous body, and then cross-linking collagen in said porous body.

2. The method for producing a cross-linked apatite/collagen porous body according to claim 1, wherein said apatite/collagen composite is produced by simultaneously dropping an aqueous solution of phosphoric acid or a salt thereof containing collagen and an aqueous solution or suspension of a calcium salt into water.

3. The method for producing a cross-linked apatite/collagen porous body according to claim 1, wherein a ratio of said apatite/collagen composite to said collagen is 97/3 to 93/7 by mass in said dispersion.

4. The method for producing a cross-linked apatite/collagen porous body according to claim 1, wherein an apatite/collagen ratio is 9/1 to 6/4 by mass in said apatite/collagen composite.

5. The method for producing a cross-linked apatite/collagen porous body according to claim 1, wherein said dispersion is kept at a temperature of 35° C. to 43° C. for gelation.

6. The method for producing a cross-linked apatite/collagen porous body according to claim 1, wherein said dispersion is gelled after its pH is adjusted to 7.0 to 7.4.

7. The method for producing a cross-linked apatite/collagen porous body according to claim 1, wherein said dispersion is gelled after the ionic strength of said dispersion is adjusted to 0.2 to 0.8.

8. The method for producing a cross-linked apatite/collagen porous body according to claim 1, wherein said apatite/collagen composite is in the form of fibers of 1 mm or less in length.

9. The method for producing a cross-linked apatite/collagen porous body according to claim 1, wherein apatite in said apatite/collagen composite has a C-axis oriented along the collagen fibers.

10. The method for producing a cross-linked apatite/collagen porous body according to claim 1, wherein apatite in said cross-linked apatite/collagen porous body has a C-axis oriented along the collagen fibers.

11. The method for producing a cross-linked apatite/collagen porous body according to claim 1, wherein apatite in said apatite/collagen composite is hydroxyapatite.

12. A cross-linked apatite/collagen porous body produced by the method recited in claim 1.

13. The method for producing a cross-linked apatite/collagen porous body according to claim 1, wherein said apatite/collagen composite is produced by freeze-drying a mixture obtained by simultaneously dropping an aqueous solution of phosphoric acid or a salt thereof containing collagen and an aqueous solution or suspension of a calcium salt into water.

* * * * *